United States Patent [19]

Anhäuser et al.

[11] Patent Number: 5,516,395

[45] Date of Patent: May 14, 1996

[54] PROCESS FOR THE PRODUCTION OF COLLAGEN FOAMS IN THE FORM OF CONTINUOUS TAPES AND THEIR USE IN MEDICINE, COSMETICS AND HYGIENE

[75] Inventors: Dieter Anhäuser, Melsbach; Michael Roreger, Neuwied, both of Germany

[73] Assignee: LTS Lohmann Therapie-Systeme GmbH & Co. KG, Neuwied, Germany

[21] Appl. No.: 172,403

[22] Filed: Dec. 23, 1993

Related U.S. Application Data

[63] Continuation-in-part of Ser. No. 655,265, Feb. 13, 1991, abandoned, which is a continuation of Ser. No. 408,816, Sep. 18, 1989, abandoned.

[30] Foreign Application Priority Data

Sep. 22, 1988 [DE] Germany ............................ 38 32 162.9

[51] Int. Cl.$^6$ .................................................... B32B 31/00
[52] U.S. Cl. .......................... 156/242; 156/259; 585/813; 82/1.11; 82/101; 264/158
[58] Field of Search .................................... 264/158, 160, 264/159, 157, 28, 138, 45.6; 128/888; 82/1.11, 101; 585/813; 602/43; 156/247, 259, 242

[56] References Cited

U.S. PATENT DOCUMENTS

| | | |
|---|---|---|
| 2,158,086 | 5/1939 | Roberts . |
| 3,157,524 | 11/1964 | Artandi . |
| 3,800,792 | 4/1974 | McKnight . |
| 4,243,625 | 1/1981 | Burge . |
| 4,320,201 | 3/1982 | Berg . |
| 4,505,855 | 3/1985 | Bruns . |
| 4,789,401 | 12/1988 | Ebinger . |
| 4,815,457 | 3/1989 | Mazars . |
| 4,861,714 | 8/1989 | Dean, Jr. . |

*Primary Examiner*—Chester T. Barry
*Attorney, Agent, or Firm*—Sprung Horn Kramer & Woods

[57] ABSTRACT

The present invention relates to a process for the production of collagen foams in the form of continuous tapes, characterized in that a) solved or dispersed collagen is cast into disk molds, b) the collagen solution or dispersion is frozen in the disk mold and subsequently is freeze-dried c) continuous tapes are produced from the freeze-dried disks by mechanical processes. Furthermore, the present invention relates to the use of said tapes so obtained in medicine, cosmetic and hygiene.

12 Claims, No Drawings

PROCESS FOR THE PRODUCTION OF COLLAGEN FOAMS IN THE FORM OF CONTINUOUS TAPES AND THEIR USE IN MEDICINE, COSMETICS AND HYGIENE

This application is a continuation-in-part of application Ser. No. 07/655,265, filed Feb. 13, 1991, now abandoned, which is a continuation of Ser. No. 07/408,816, filed on Sept. 18, 1989, now abandoned.

It is known that in medicine, cosmetics and hygiene collagen foams or collagenous nonwovens having excellent compatibility with the skin and mucous membranes are used. One reason is the intrinsic effect of collagen, another is the good absorption and cushioning or padding effect of collagen foams, e.g. in medicine for local hemostasis, as wound dressing having wound-healing promoting properties, as filling material for bone cavities, or as resorbable active substance carriers for implants.

Processes for the production of such collagen foams having spongy or nonwoven structure for the mentioned purposes by the freeze drying of collagen solutions or dispersions have long been known (e.g., EP 209 726 Beutler/Ebinger/Lindner, DE patent publication 32 03 957 Eckmayer, U.S. Pat. No. 3,157,524 Artandi, DE 29 43 520 Berg/Eckmayer, DE patent publication 33 15 678 Ciocar, DE 18 11 290 Chvapil). According to these processes collagen solutions or dispersions are cast into containers and freeze-dried therein. Form and dimension of the freeze dried collagen foams are determined by the form and dimension of the containers. Confection of these foams either takes place directly within the containers or after removing them therefrom. A disadvantage of these processes is that due to the individual manufacture of each foam, all further processing steps after the freeze drying are very time consuming and thus costly. The number of final products per time unit is very low.

A further possibility is to freeze-dry collagen solutions or dispersions by adding tanning or cross-linking agents over a large surface in corresponding containers, and subsequently produce from these freeze-dried plates collagen foams of a defined size by means of splitting, cutting, and/or punching. A disadvantage of this process, on the one hand, is that the large surface foams have to be stabilized by tanning or cross-linking the collagen in order to achieve the necessary strength for further processing, and, on the other hand, the further processing of such foams is carried out discontinuously and requires high staff and time expense.

Collagen, Native collagen, Collagen Solution and Dispersion Addition of Active Substances The collagen used according to the present invention preferably derives from the skin of young calves which is dehaired and degreased at first. Then, the soluble collagen and non-collagen components of the connective tissue are extracted. The telopeptides are split from the remaining collagens being insoluble in water, said telopeptides being responsible for the antigenic properties of the collagen, and a defined part of the intermolecular collagen bonds is split by a correspondingly controlled process. The intramolecular bonds of the collagen are not affected so that the helical structure of the molecule is not damaged.

This splitting or cleavage can be carried out in such a way that a major part of the collagen is rendered water-soluble so that after filtration or centrifugation a solution is obtained which is free of insoluble collagen. If the cleavage is controlled such that only a small amount of intermolecular bonds is split, mainly higher molecular, water-insoluble collagen aggregates are obtained which are dispersed in water. A stable dispersion contains up to approximately 5%-wt, preferably up to 2%-wt, collagen in uniform distribution. For the production of freeze-dried collagen foams with high mechanical strength preferably dispersions having a very high content of high molecular aggregates are used, since, due to the high natural cross-linking rate of the collagen, the foam is stabilized. This is advantageous because additional manipulations to strengthen the foam, such as, e.g. tannage or cross-linking, become superfluous and the original quaternary structure of the collagen, like that in the skin, mainly is retained.

Further active substances, preferably medical ones, e.g. antiseptics or antibiotics, as well as further auxiliaries can be incorporated into the collagen preparation (solution or dispersion). If the collagen preparation is to be used for the production of sterile products for medical purposes, the collagen isolation process is carried out such that the collagen preparation obtained is sterile.

Filling, Freeze-drying, Disk Molds Pre-Treatment of the Disks

The collagen preparation is filled into disk molds of optional, preferably round shape having any height between 0.5 and 10 cm, preferably between 1 and 4 cm, and any diameter, preferably between 50 and 70 cm, whereby the filling height of the collagen preparation in the mold is chosen such that the preparation does not splash over the rim of the mold when the mold is transported and introduced into the freeze-dryer. The term disk in the sense of the present invention means a form the thickness of which is small relative to its diameter. If the collagen sponge obtained by the freeze-drying shall be further processed in a later process step on a peeling machine, the collagen preparation is preferably cast into a disk mold which has a central slot of optional, preferably round shape having any diameter, preferably between 1 and 10 cm. In this case, the collagen foam, after freeze-drying, is provided with a central hole the diameter of which preferably is a bit smaller than the diameter of the hub of the peeling machine, in order to prevent the collagen foams from slipping aside during the peeling process. The collagen preparation in the disk mold is shock-frozen in a deepfreeze cabinet or in the freeze-dryer with a high temperature depression rate (freezing rate) to temperatures of less than or equal to $-50°$ C. to form as small ice crystals as possible, so that the structure of the pores in the finished foam is fine and uniform. The deepfrozen collagen preparation is then freeze-dried under vacuum, whereby the drying time up to achieving a product temperature of about $30°$ C. is in the range of 12 h and 60 h, depending on the layer thickness of the freeze-dried pieces.

Since the collagen foams frequently exhibit an irregular surface structure after freeze-drying, they are adjusted to a defined thickness prior to further processing. A central hole is cut or punched in the collagen foam, if a mold without a central slot has been used for freeze-drying, and if the further processing is to be carried out by means of the peeling process.

EXAMPLE 9.0 kg native collagen dispersion 0.75% (filling height in the mold appr. 35 mm) is cast into disk molds (circular bottom plate having 580 mm diameter, externally surrounding rim of 45 mm height, internal circular slot of 83 mm diameter, and a web height of 45 mm). The dispersion in the mold was shock-frozen in the freeze dryer, and subsequently freeze-dried in the vacuum for appr. 48 h. After termination of the drying, wheel-shaped collagen disks of 25 mm thickness were obtained. Several of these collagen disks were pushed side by side, horizontally with the central bore onto the ribbed peeling axis of a band knife peeling machine. Then, tapes of appr. 3 mm thickness are peeled to a length of appr. 70 m from the collagen disks and automatically wound up on the hub.

For the production of a first-aid dressing having a continuous wound pad the collagen tape having 25 mm width is lamination coated on a confection machine centrally onto a textile carrier having been rendered self-adhesive; subsequently it is covered and punched to a 60×20 mm format and finished.

As employed hereinabove, "shock freezing" is a translation of the German term "schockgefrieren". It is a synonym of cryo-transfer. According to German handbook by Pohlmann, Taschenbuch fur Kaltetechnik. Verlag C. F. Müller, Karlsruhe 1988, 17th Edition, Chapter 10, line 1, page 567 states, in translation:

"The higher the freezing speed, the smallest and more even is the structure of the ice crystals in the cells and in the tissue between".

Another passage of such handbook states:

"The mechanical damages (deterioration) of the cell tissue occurring by the large-sized ice cells formed on slow freezing are an indication against this process; such damages are not observed with the small crystals formed in the case of a quick ice formation".

Advantageously the shock freezing in accordance with the present invention is effected in a manner so that the freezing rate is about 30° C., hour or higher; thus freezing from room temperature to about −40° C. or lower is advantageously effected in about 2 hours.

The importance of such extremely fast cooling is shown in the following illustrative example:

Comparison Example

Samples of aqueous collagen dispersions containing 0.75% collagen were filled in polystyrene blisters of 12×8×1.5 cm such that each blister contained 93 g of dispersion, corresponding to a filling height of 0.8 cm. The dispersions had an initial temperature of +25° C. They were frozen in separate tests to a temperature of −40° C. Series A was brought to this temperature with a temperature decrease rate of 30° C./hour, while Series B was subjected to a temperature decrease rate of 20° C./hour. In order to achieve a temperature decrease rate of 30° C., the collagen dispersions were introduced into a lyophilisator in which the sole had a temperature of −50° C., while in Series B the collagen dispersion was introduced into the lyophilisator at ambient temperature (about 20° C.), and subsequently the whole system was cooled to a temperature of below −40° C.

Thus, the period for completely cooling down the dispersion to a block having a temperature of less than −40° C. in Series A was about two hours compared with three hours in Series B.

Results

In both series a collagen foam was produced. However, while the pores of the foams obtained by the process of Series A were very small and even, the pores of the product obtained by the process of Series B were uneven and the product in part had very large-sized pores, so that a sponge was obtained which could not be processed since the pores were by far too large so that the sponge could not be cut into products of the desired size and quality since the sponge immediately tore at the sites of the large-sized pores (holes).

It will be understood that the specification and examples are illustrative but not limitative of the present invention and that other embodiments within the spirit and scope of the invention will suggest themselves to those skilled in the art.

We claim:

1. A process for the production of a collagen foam in the form of a plurality of continuous tapes, comprising
   a) casting dissolved or dispersed native uncross-linked collagen manufactured from animal skin into a disk mold to a height of about 0.5 to 10 cm,
   b) shock-freezing the collagen solutions or dispersions in the disk mold to a temperature of −50° C. or lower at a rate of at least about 30° C./hour, and then freeze-drying under vacuum, thereby forming a plurality of homogeneous sponges having very fine pores and disc shapes, and
   c) placing the discs side by side vertically on a hub and mechanically peeling a plurality of continuous tapes from the freeze-dried collagen on a tape peeling machine.

2. A process according to claim 1, wherein the collagen concentration in the solution or dispersion is about 0.1 to 5 percent by weight.

3. A process according to claim 1, wherein the collagen concentration in the solution or dispersion is about 0.5 to 2 percent by weight.

4. A process according to claim 1, wherein the collagen is native, uncross-linked collagen manufactured from the skin of young calves.

5. A process according to claim 1, wherein the disk mold is from about 0.5 to 10 cm in height and from about 50 to 70 cm in diameter.

6. A process according to claim 1, wherein the disk mold is from about 1 to 4 cm in height and from about 50 to 70 cm in diameter.

7. A process according to claim 1, wherein the disk mold is provided with a central opening so that the collagen foam disk after freeze drying has a central hole.

8. A process according to claim 1, wherein the disk mold has no central opening, and wherein a central hole is punched or cut from the freeze-dried collagen foam.

9. A process according to claim 1, wherein the freeze-dried collagen foam of step (b) is cut to a predetermined thickness prior to step (c).

10. A process according to claim 1, wherein the peeled tape is about 1 to 5 mm in thickness and of the order of 70 m in length.

11. A process according to claim 1, including a further step of coating or laminating the tape.

12. A process according to claim 1, wherein the collagen tape is put on a carrier which has been rendered self-adhesive, a covering is applied which is provided with at least one of a stripping off and application aid, and the material so obtained is cut to a predetermined size, suitable for a first-aid or wound dressing.

* * * * *